(12) United States Patent
Ding et al.

(10) Patent No.: US 7,491,233 B1
(45) Date of Patent: Feb. 17, 2009

(54) PURIFIED POLYMERS FOR COATINGS OF IMPLANTABLE MEDICAL DEVICES

(75) Inventors: Ni Ding, San Jose, CA (US); Wouter E Roorda, Palo Alto, CA (US)

(73) Assignee: Advanced Cardiovascular Systems Inc., Santa Clara, CA (US)

( * ) Notice: Subject to any disclaimer, the term of this patent is extended or adjusted under 35 U.S.C. 154(b) by 207 days.

(21) Appl. No.: 10/198,912

(22) Filed: Jul. 19, 2002

(51) Int. Cl.
*A61F 2/06* (2006.01)
(52) U.S. Cl. .................................. 623/1.42; 427/2.28
(58) Field of Classification Search .............. 623/1.14, 623/1.18, 1.21, 1.42, 1.43, 1.46; 427/2.28
See application file for complete search history.

(56) References Cited

U.S. PATENT DOCUMENTS

| | | |
|---|---|---|
| 2,968,649 A | 1/1961 | Pailthorp et al. |
| 3,051,677 A | 8/1962 | Rexford |
| 3,178,399 A | 4/1965 | Lo |
| 3,324,069 A | 6/1967 | Koblitz et al. |
| 3,779,805 A | 12/1973 | Alsberg |
| 3,856,827 A | 12/1974 | Cavitt |
| 4,076,929 A | 2/1978 | Dohany |
| 4,197,380 A | 4/1980 | Chao et al. |
| 4,304,010 A | 12/1981 | Mano |
| 4,346,710 A | 8/1982 | Thanawalla et al. |
| 4,353,960 A | 10/1982 | Endo et al. |
| 4,399,264 A | 8/1983 | Squire |
| 4,413,359 A | 11/1983 | Akiyama et al. |
| 4,423,183 A | 12/1983 | Close |
| 4,485,250 A | 11/1984 | Squire |
| 4,530,569 A | 7/1985 | Squire |
| 4,564,013 A | 1/1986 | Lilenfeld et al. |
| 4,569,978 A | 2/1986 | Barber |
| 4,632,842 A | 12/1986 | Karwoski et al. |
| 4,636,346 A | 1/1987 | Gold et al. |
| 4,718,907 A | 1/1988 | Karwoski et al. |
| 4,733,665 A | 3/1988 | Palmaz |
| 4,749,585 A | 6/1988 | Greco et al. |
| 4,754,009 A | 6/1988 | Squire |
| 4,770,939 A | 9/1988 | Sietsess et al. |
| 4,800,882 A | 1/1989 | Gianturco |
| 4,871,357 A | 10/1989 | Hsu et al. |
| 4,876,109 A | 10/1989 | Mayer et al. |
| 4,886,062 A | 12/1989 | Wiktor |
| 4,897,457 A | 1/1990 | Nakamura et al. |

(Continued)

FOREIGN PATENT DOCUMENTS

DE     19723723 A1     12/1998

(Continued)

OTHER PUBLICATIONS

Fourier Transform Infrared Spectroscopy, *Determination of Plasticisers in PVC*, Chem 3041 Manual, pp. 51-55.

(Continued)

*Primary Examiner*—Kevin T Truong
*Assistant Examiner*—Victor X Nguyen
(74) *Attorney, Agent, or Firm*—Squire, Sanders & Dempsey L.L.P.

(57) ABSTRACT

A coating for a medical device, particularly for a drug eluting stent, is described. The coating includes a purified polymer such as a polyacrylate.

23 Claims, 5 Drawing Sheets

U.S. PATENT DOCUMENTS

| | | | |
|---|---|---|---|
| 4,908,404 A | 3/1990 | Benedict et al. | |
| 4,910,276 A | 3/1990 | Nakamura et al. | |
| 4,931,287 A | 6/1990 | Bae et al. | |
| 4,935,477 A | 6/1990 | Squire | |
| 4,948,851 A | 8/1990 | Squire | |
| 4,973,142 A | 11/1990 | Squire | |
| 4,975,505 A | 12/1990 | Squire | |
| 4,977,008 A | 12/1990 | Squire | |
| 4,977,025 A | 12/1990 | Squire | |
| 4,977,026 A | 12/1990 | Squire | |
| 4,977,297 A | 12/1990 | Squire | |
| 4,977,901 A | 12/1990 | Ofstead | 128/772 |
| 4,982,056 A | 1/1991 | Squire | |
| 4,985,308 A | 1/1991 | Squire | |
| 4,990,222 A | 2/1991 | Aigner et al. | 203/91 |
| 4,999,248 A | 3/1991 | Squire | |
| 5,000,547 A | 3/1991 | Squire | |
| 5,006,382 A | 4/1991 | Squire | |
| 5,030,394 A | 7/1991 | Sietses et al. | |
| 5,047,020 A | 9/1991 | Hsu | |
| 5,051,114 A | 9/1991 | Nemser et al. | |
| 5,051,978 A | 9/1991 | Mayer et al. | |
| 5,053,048 A | 10/1991 | Pinchuk | |
| 5,076,659 A | 12/1991 | Bekiarian et al. | |
| 5,093,427 A | 3/1992 | Barber | |
| 5,107,852 A | 4/1992 | Davidson et al. | |
| 5,110,645 A | 5/1992 | Matsumoto et al. | |
| 5,112,457 A | 5/1992 | Marchant | 204/165 |
| 5,176,972 A | 1/1993 | Bloom et al. | |
| 5,185,408 A | 2/1993 | Tang et al. | |
| 5,246,451 A | 9/1993 | Trescony et al. | |
| 5,276,121 A | 1/1994 | Resnick | |
| 5,296,283 A | 3/1994 | Froggatt | |
| 5,302,385 A | 4/1994 | Khan et al. | |
| 5,308,685 A | 5/1994 | Froggatt | |
| 5,310,838 A | 5/1994 | Hung et al. | |
| 5,324,889 A | 6/1994 | Resnick | |
| 5,326,839 A | 7/1994 | Resnick | |
| 5,328,471 A | 7/1994 | Slepian | 604/101 |
| 5,336,518 A | 8/1994 | Narayanan et al. | |
| 5,338,608 A | 8/1994 | Resnick | |
| 5,342,348 A | 8/1994 | Kaplan | |
| 5,353,368 A | 10/1994 | Resnick | |
| 5,354,910 A | 10/1994 | Hung et al. | |
| 5,368,566 A | 11/1994 | Crocker | |
| 5,380,299 A | 1/1995 | Fearnot et al. | |
| 5,383,853 A | 1/1995 | Jung et al. | |
| 5,383,928 A | 1/1995 | Scott et al. | |
| 5,395,311 A | 3/1995 | Andrews | |
| 5,403,341 A | 4/1995 | Solar | |
| 5,408,020 A | 4/1995 | Hung et al. | |
| 5,417,969 A | 5/1995 | Hsu et al. | |
| 5,443,458 A | 8/1995 | Eury | |
| 5,447,724 A | 9/1995 | Helmus et al. | |
| 5,455,040 A | 10/1995 | Marchant | 424/426 |
| 5,464,650 A | 11/1995 | Berg et al. | 427/2.3 |
| 5,545,208 A | 8/1996 | Wolff et al. | |
| 5,560,463 A | 10/1996 | Link et al. | |
| 5,562,734 A | 10/1996 | King | 623/16 |
| 5,569,463 A | 10/1996 | Helmus et al. | |
| 5,575,818 A | 11/1996 | Pinchuk | |
| 5,578,073 A | 11/1996 | Haimovich et al. | 623/1 |
| 5,584,877 A | 12/1996 | Miyake et al. | 623/1 |
| 5,591,224 A | 1/1997 | Schwartz et al. | |
| 5,604,283 A | 2/1997 | Wada et al. | |
| 5,605,696 A | 2/1997 | Eury et al. | 424/423 |
| 5,616,608 A | 4/1997 | Kinsella et al. | |
| 5,628,728 A | 5/1997 | Tachibana et al. | |
| 5,632,771 A | 5/1997 | Boatman et al. | |
| 5,632,776 A | 5/1997 | Kurumatani et al. | |
| 5,632,840 A | 5/1997 | Campbell | |
| 5,635,201 A | 6/1997 | Fabo | |
| 5,667,767 A | 9/1997 | Greff et al. | 424/9.411 |
| 5,670,558 A | 9/1997 | Onishi et al. | 523/112 |
| 5,679,400 A * | 10/1997 | Tuch | 427/2.14 |
| 5,684,061 A | 11/1997 | Ohnishi et al. | |
| 5,691,311 A | 11/1997 | Maraganore et al. | |
| 5,697,967 A | 12/1997 | Dinh et al. | |
| 5,700,286 A | 12/1997 | Tartaglia et al. | 623/1 |
| 5,713,949 A | 2/1998 | Jayaraman | |
| 5,716,981 A | 2/1998 | Hunter et al. | 514/449 |
| 5,750,234 A | 5/1998 | Johnson et al. | |
| 5,758,205 A | 5/1998 | Hara et al. | |
| 5,759,205 A | 6/1998 | Valentini | 623/16 |
| 5,760,118 A | 6/1998 | Sinclair et al. | |
| 5,776,184 A | 7/1998 | Tuch | |
| 5,804,318 A | 9/1998 | Pinchuk et al. | |
| 5,817,727 A | 10/1998 | Prass et al. | 526/328 |
| 5,820,917 A | 10/1998 | Tuch | |
| 5,824,048 A | 10/1998 | Tuch | |
| 5,824,049 A | 10/1998 | Ragheb et al. | 623/1 |
| 5,827,587 A | 10/1998 | Fukushi | |
| 5,830,178 A | 11/1998 | Jones et al. | 604/49 |
| 5,837,008 A | 11/1998 | Berg et al. | |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,858,990 A | 1/1999 | Walsh | |
| 5,860,963 A | 1/1999 | Azam et al. | |
| 5,861,168 A | 1/1999 | Cooke et al. | |
| 5,865,814 A | 2/1999 | Tuch | 604/265 |
| 5,869,127 A | 2/1999 | Zhong | |
| 5,873,904 A | 2/1999 | Ragheb et al. | 623/1 |
| 5,874,165 A | 2/1999 | Drumheller | |
| 5,879,697 A | 3/1999 | Ding et al. | |
| 5,897,911 A | 4/1999 | Loeffer | |
| 5,900,425 A | 5/1999 | Kanikanti et al. | |
| 5,911,704 A | 6/1999 | Humes | |
| 5,921,933 A | 7/1999 | Sarkis et al. | |
| 5,922,393 A | 7/1999 | Jayaraman | |
| 5,928,279 A | 7/1999 | Shannon et al. | |
| 5,932,299 A | 8/1999 | Katoot | |
| 5,945,115 A | 8/1999 | Dunn et al. | |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | |
| 6,015,541 A | 1/2000 | Greff et al. | 424/1.25 |
| 6,033,724 A | 3/2000 | Molitor | |
| 6,042,875 A | 3/2000 | Ding et al. | 427/2.24 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,534 A | 5/2000 | Ronan et al. | |
| 6,080,488 A | 6/2000 | Hostettler et al. | 428/423.3 |
| 6,090,134 A | 7/2000 | Tu et al. | |
| 6,096,070 A | 8/2000 | Ragheb et al. | 623/1 |
| 6,096,396 A | 8/2000 | Patton et al. | |
| 6,096,798 A | 8/2000 | Luthra et al. | |
| 6,096,809 A | 8/2000 | Lorcks et al. | |
| 6,099,562 A | 8/2000 | Ding et al. | 623/1.46 |
| 6,099,563 A | 8/2000 | Zhong | |
| 6,110,188 A | 8/2000 | Narciso, Jr. | 606/153 |
| 6,110,483 A | 8/2000 | Whitbourne et al. | |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,124,045 A | 9/2000 | Soda et al. | |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,179,817 B1 | 1/2001 | Zhong | |
| 6,197,051 B1 | 3/2001 | Zhong | |

| | | | |
|---|---|---|---|
| 6,203,551 B1 | 3/2001 | Wu | |
| 6,214,901 B1 | 4/2001 | Chudzik et al. | |
| 6,224,894 B1 | 5/2001 | Jamiolkowski et al. | |
| 6,231,590 B1 | 5/2001 | Slaikeu et al. | |
| 6,242,041 B1 | 6/2001 | Katoot et al. | |
| 6,254,632 B1 | 7/2001 | Wu et al. | |
| 6,258,121 B1 | 7/2001 | Yang et al. | |
| 6,262,034 B1 | 7/2001 | Mathiowitz et al. | |
| 6,273,913 B1 | 8/2001 | Wright et al. | |
| 6,299,604 B1 | 10/2001 | Ragheb et al. | |
| 6,344,035 B1 | 2/2002 | Chudzik | |
| 6,362,271 B1 | 3/2002 | Lin et al. | |
| 6,408,878 B2 | 6/2002 | Unger et al. | |
| 6,410,612 B1 | 6/2002 | Hatanaka | |
| 6,464,683 B1 | 10/2002 | Samuelson et al. | |
| 6,503,556 B2 | 1/2003 | Harish et al. | |
| 6,545,097 B2 | 4/2003 | Pinchuk et al. | |
| 6,551,708 B2 | 4/2003 | Tsuda et al. | |
| 6,716,444 B1 * | 4/2004 | Castro et al. | 424/422 |
| 6,746,773 B2 | 6/2004 | Llanos et al. | |
| 2001/0014717 A1 | 8/2001 | Hossainy et al. | |
| 2001/0029351 A1 | 10/2001 | Falotico et al. | |
| 2002/0051730 A1 | 5/2002 | Bodnar et al. | |
| 2002/0090389 A1 | 7/2002 | Humes et al. | |
| 2002/0091211 A1 * | 7/2002 | Chung | 526/196 |
| 2002/0094440 A1 | 7/2002 | Llanos et al. | 428/421 |
| 2002/0099438 A1 | 7/2002 | Furst | |
| 2002/0111590 A1 | 8/2002 | Davila et al. | 604/265 |
| 2002/0122877 A1 | 9/2002 | Harish et al. | |
| 2002/0123801 A1 | 9/2002 | Pacetti et al. | |
| 2002/0133183 A1 | 9/2002 | Lentz et al. | |
| 2002/0143386 A1 | 10/2002 | Davila et al. | |
| 2002/0165608 A1 | 11/2002 | Llanos et al. | |
| 2002/0188037 A1 | 12/2002 | Chudzik et al. | |
| 2003/0004563 A1 | 1/2003 | Jackson et al. | |
| 2003/0031780 A1 | 2/2003 | Chudzik et al. | |
| 2003/0039689 A1 | 2/2003 | Chen et al. | |
| 2003/0060877 A1 | 3/2003 | Falotico et al. | |
| 2003/0065346 A1 | 4/2003 | Evens et al. | |
| 2003/0065377 A1 | 4/2003 | Davila et al. | |
| 2003/0073961 A1 | 4/2003 | Happ | |
| 2003/0077312 A1 | 4/2003 | Schmulewicz et al. | |
| 2004/0063805 A1 | 4/2004 | Pacetti et al. | |
| 2004/0102758 A1 | 5/2004 | Davila et al. | |

FOREIGN PATENT DOCUMENTS

| | | | |
|---|---|---|---|
| EP | 0568310 A1 | 11/1993 | |
| EP | 0623354 A1 | 11/1994 | |
| EP | 0633032 A1 | 1/1995 | |
| EP | 0 665 023 | 8/1995 | |
| EP | 0747069 A2 | 12/1996 | |
| EP | 0815803 A1 | 1/1998 | |
| EP | 0893108 A2 | 1/1999 | |
| EP | 0950385 A2 | 10/1999 | |
| EP | 0950386 A2 | 10/1999 | |
| EP | 0 970 711 | 1/2000 | |
| EP | 0968688 A1 | 1/2000 | |
| EP | 1 023 879 | 2/2000 | |
| EP | 0997115 A2 | 5/2000 | |
| EP | 1 192 957 | 3/2002 | |
| WO | WO 92/05695 | 4/1992 | |
| WO | WO 92/18320 | 10/1992 | |
| WO | WO 94/02185 | 2/1994 | |
| WO | WO 96/21404 | 7/1996 | |
| WO | WO 97/41164 | 11/1997 | |
| WO | WO 98/08463 | 3/1998 | |
| WO | WO 98/13405 | 4/1998 | |
| WO | WO 98/36784 | 8/1998 | |
| WO | WO 98/58680 | 12/1998 | |
| WO | WO 99/32051 | 7/1999 | |
| WO | WO 99/55396 | 11/1999 | |
| WO | WO 00/02599 * | 1/2000 | |
| WO | WO 00/12147 | 3/2000 | |
| WO | WO 00/27455 | 5/2000 | |
| WO | WO 00/29043 | 5/2000 | |
| WO | WO 00/32255 | 6/2000 | |
| WO | WO 00/38754 | 7/2000 | |
| WO | WO 00/41738 | 7/2000 | |
| WO | WO 00/64506 | 11/2000 | |
| WO | WO 01/01890 | 1/2001 | |
| WO | WO 01/30403 A1 | 5/2001 | |
| WO | WO 01/49340 | 7/2001 | |
| WO | WO 01/87342 A2 | 11/2001 | |
| WO | WO 01/87368 | 11/2001 | |
| WO | WO 01/87372 A1 | 11/2001 | |
| WO | WO 01/87376 A1 | 11/2001 | |
| WO | WO 02/24249 | 3/2002 | |
| WO | WO 02/26139 A1 | 4/2002 | |
| WO | WO 02/26271 A | 4/2002 | |
| WO | WO 02/26281 A1 | 4/2002 | |
| WO | WO 02/47731 | 6/2002 | |
| WO | WO 02/47732 | 6/2002 | |
| WO | WO 03/022324 | 3/2003 | |

OTHER PUBLICATIONS

Precision™ Pure Solvents, Purification Technologies Inc., *Methanol—HPLC Grade*, http://www.purificationtech.com/mth/htm, printed Jul. 1, 2002 (2 pages).

Suzuki et al., *Stent-Based Delivery of Sirolimus Reduces Neointimal Formation in a Porcine Coronary Model*, Circulation 104(10):1188 (12 pages).

U.S. Appl. No. 09/966,036, filed Sep. 28, 2001, Happ.

U.S. Appl. No. 10/176,504, filed Jun. 21, 2002, Roorda et al.

U.S. Appl. No. 10/176,510, filed Jun. 21, 2002, Hossainy et al.

U.S. Appl. No. 10/177,117, filed Jun. 21, 2002, Hossainy.

U.S. Appl. No. 10/177,154, filed Jun. 21, 2002, Hossainy et al.

U.S. Appl. No. 10/320,899, filed Dec. 16, 2002, Shah et al.

U.S. Appl. No. 10/376,348, filed Feb. 26, 2003, Ding et al.

U.S. Appl. No. 10/428,691, filed May 1, 2003, Pacetti.

U.S. Appl. No. 10/931,927, filed Aug. 31, 2004, Pacetti.

Anonymous, *Rolling Therapeutic Agent Loading Device for Therapeutic Agent Delivery of Coated Stent*, Research Disclosure, Publ., Hampshire, GB, No. 434, p. 975 (2002).

Arnold et al., *Effects of environment on the creep properties of a poly(ethylmethacrylate) based bone cement* J. Mater Sci: Mater. In Med., vol. 12, pp. 707-717 (2001).

Bellex International, *CYTOP®, Amorphous Fluorocarbon Polymer*, 1 page (no date).

Bellex International, *Selected CYTOP Physical Data*, 1 page (no date).

Bellex International, *CYTOP®*, http://www.bellexinternational.com/cytop.htm, printed Mar. 30, 2001, 1 page.

Dalsin et al., *DOPA: A New Anchor for PEGylation of Biomaterial Surfaces*, Soc. For Biomaterials 28th Annual Meeting Transactions, pp. 40 (2002).

Deb et al., *Effect of crosslinking agents on poly(ethylmethacrylate) bone cements*, J. of Mater.Sci: Mater. In Med., vol. 8, pp. 829-833 (1997).

Del Guerra et al., *In vitro biocompatibility of fluorinated polyurethanes*, J. Mater. Sci. in Med., vol. 5, pp. 452-456 (1994).

DuPont, *Teflon AF 1601S amorphous fluoropolymer solutions*, product information, 2 pages (1998).

DuPont, *Processing of Teflon® AF*, Teflon Amorphous Fluoropolymer, http://www.dupont.com/teflon/af/processing.html, printed Mar. 30, 2001, 1 page.

DuPont, *High-Performance/Potential Applications*, Teflon Amorphous Fluoropolymer, http://www.dupont.com/teflon/af/potapps.html, printed Mar. 30, 2001, 3 pages.

DuPont, *Performance Comparison of Teflon AF*, Teflon Amorphous Fluoropolymer, http://www.dupont.com/teflon/af/performance.html, printed Mar. 30, 2001, 3 pages.

DuPont, *Unique Properties of Teflon® AF*, Teflon Amorphous Fluoropolymer, http://www.dupont.com/teflon/af/unique.html, printed Mar. 30, 2001, 3 pages.

DuPont, *Teflon® AF: A New Generation of High-Performance Fluoropolymer Resins*, http://www.dupont.com/teflon/af/index.html, printed Mar. 30, 2001, 1 page.

DuPont, *Teflon® Protects Superconductors Against Acid*, Teflon Amorphous Fluoropolymer, http://www.dupont.com/teflon/af/superconductor.html, printed Sep. 21, 2004, 2 pages.

DuPont, *Available Grades of DuPont Teflon® AF*, Teflon Amorphous Fluoropolymer, http://www.dupont.com/teflon/af/grades.html, printed Sep. 21, 2004, 2 pages.

DuPont, *Teflon® AF amorphous fluoropolymers*, Product Information, 6 pages (1998).

DuPont, Sales Notice, Teflon Amorphous Fluoropolymer, http://www.dupont.com/teflon/af/patent.html, printed Sep. 21, 2004, 2 pages.

Fine et al., *Improved nerve regeneration through piezoelectric vinylidenefluoride- trifluoroethylene copolymer guidance channels*, Biomaterials, vol. 12, Oct., pp. 775-780 (1991).

Fischell, *Polymer Coatings for Stents*, Circulation, 94:1494-95 (1996).

Gullickson, *Reference Data Sheet on Common Chlorinated Solvents*, http://www.mcs.net/~hutter/tee/chlorina.html, printed Mar. 30, 2001, 5 pages.

Gunn et al., *Stent coatings and local drug delivery*, Eur. Heart J., vol. 20, issue 23, pp. 1693-1700 (1999).

Harper et al., *Fatigue Characteristics of Polyethylmethacrylate Based Bone Cement Reinforced with Silane Coupled Hydroxyapatite*, Fifth World Biomaterials Congress, May 29-Jun. 2, 1996, Toronto, Canada, Abstract 351, 3 pgs.

Harper et al., *Mechanical properties of hydroxyapatite reinforced poly (ethyl methacrylate) bone cement after immersion in a physiological solution: influence of a silane coupling agent*, J. Mater. Sci.: Mater. In Med., vol. 11, pp. 491-497 (2000).

Kruft et al., *Studies on radio-opaque polymeric biomaterials with potential applications to endovascular prostheses*, Biomaterials, vol. 17, No. 18, pp. 1803-1812 (1996).

Lambert et al., *Localized Arterial Wall Drug Delivery From a Polymer-Coated Removable Metallic Stent*, Circulation, vol. 90, No. 2, pp. 1003-1011 (1994).

Laroche et al., *Polyvinylidene fluoride (PVDF) as a biomaterial: From polymeric raw material to monofilament vascular suture*, J. of Biomedical Mat. Research, vol. 29, pp. 1525-1536 (1995).

Lin et al., *Fluropolymer Alloys Performance Optimization of PVDF Alloys*, Fluropolymers 2 Properties, edited by Hougham et al., Plenum Publishers N.Y. pp. 121-136 (1999).

Lin et al., *Surface characterization and platelet adhesion studies on fluorocarbons prepared by plasma-induced graft polymerization*, J. Biomater Sci. Polymer Edn., vol. 11, No. 7, pp. 701-714 (2000).

Luthra, Biointeractions Ltd (BIL), http://www.biomateria.com/biointeractions.html, printed Sep. 21, 2004, 3 pages.

3M, *Specialty Fluids 3M™ Fluorinert™ Liquids*, Typical Properties, http://www.3m.com/market/industrial/fluids/fluoprop.html, printed Mar. 30, 2001, 3 pages.

Materials Engineering, *Applications in Design/Manufacturing/R&D*, Materials Selector 1993, Penton Publishing (1992) 6 pgs.

Medtronic, Trillium Affinity NT, Oxygenator, Product Information, 6 pages (2000).

NCMS SOLV-DB, *Query Results for: CFC*, http://solvdb.ncms.org/CAT01.idc?chemcat=CFC, printed Mar. 30, 2001, 2 pages.

NCMS SOLV-DB, *Query Results for: FC-75 Fluorinert*, http://solvdb.ncms.org/common01.idc, printed Mar. 30, 2001, 2 pages.

Novick et al., *Protein-containing hydrophobic coatings and films*, Biomaterials, vol. 23, No. 2 (2002) pp. 441-448.

Parkell, Inc., *SNAP Powder-Liquid Temporary Crown and Bridge Resin*, http://www.parkell.com/snap.html, printed Oct. 21, 2004, 1 pg.

Parkell, Inc., *Material Safety Data Sheets*, http://www.parkell.com/msds.html, printed Oct. 21, 2004, 2 pgs.

Parkell, Inc., *MSDS No. S426, VAR, Material Safety Data Sheet*, 2 pgs (2002).

Parkell, Inc., MSDS No. S441, Material Safety Data Sheet, 2 pgs (2002).

Porté-Durrieu et al., *Surface Treatment of Biomaterials by Gamma and Swift Heavy Ions Grafting*, Nuclear Instruments and Methods in Physics Research, vol. B 151, pp. 404-415 (1999).

Porté-Durrieu et al., *Development of "Heparin-Like" Polymers Using Swift Heavy Ion and Gamma Radiation. I. Preparation and Characterization of the Materials*, Surface Treatment of Biomaterials, pp. 119-127 (2000).

Revell et al., *Experimental Studies of the Biological Response to a New Bone Cement: II Soft Tissue Reactions in the Rat*, Clinical Materials, vol. 10, pp. 233-238 (1992).

Techspray, Bulk Solvents, http://www.techspray.com/bulksup.htm, printed Sep. 21, 2004, 3 pages.

Techspray, *Flux Remover AMS*, Product Information, http://www.techspray.com/1665info.htm, printed Aug. 28, 2001, 2 pages.

Teomin et al., *Perivascular delivery of heparin for the reduction of smooth muscle cell proliferation after endothelial injury*, J. of Controlled Release, vol. 60, pp. 129-142 (1999).

Topol et al., *Frontiers in Interventional Cardiology*, Circulation, vol. 98, pp. 1802-1820 (1998).

Urban et al., *Why Make Monofilament Sutures Out of Polyvinylidene Fluoride?*, ASAIO J., vol. 40, No. 2, pp. 145-156 (1994).

Verweire et al., *Evaluation of fluorinated polymers as coronary stent coating*, J. Mater Sci: Mater. In Med., vol. 11, No. 4, pp. 207-212 (2000).

Weightman et al., *The Mechanical Properties of Cement and Loosening of the Femoral Component of Hip Replacements*, J. Bone and Joint Surg., vol. 69-B, No. 4, pp. 558-564 (Aug. 1987).

Wholey et al., *Global Experience in Cervical Carotid Artery Stent Placement*, Catherization and Cardiovascular Inteventions, vol. 50, No. 2, pp. 160-167 (2000).

Woo et al., *Phase Behavior of Polycarbonate Blends with Selected Halogenated Polymers*, J. Appl. Polym. Sci., vol. 30, pp. 4243-4249 (1985).

International Search Report for PCT appl. PCT/US03/15347, filed May 14, 2003, date of mailing Sep. 4, 2003, 6 pgs.

International Search Report for PCT appl. PCT/US03/15544, filed May 14, 2003, date of mailing Jan. 23, 2004, 9 pgs.

International Search Report for PCT appl. PCT/US03/28643, filed Sep. 10, 2003, date of mailing Mar. 12, 2003, 10 pgs.

Cifkova I. et al.: "Irritation Effects of Residual Products Derived from Poly-2-Hydroxyethyl Methacrylate Gels II. Compounds Extracted from Hydrogels", Biomaterials, vol. 9, No. 4, 1988, pp. 372-375, XP009019663, ISSN: 0142-9612, p. 3; table 3.

\* cited by examiner

PURIFIED POLYMERS FOR COATINGS OF IMPLANTABLE MEDICAL DEVICES

BACKGROUND OF THE INVENTION

1. Field of the Invention

This invention is directed to coatings for implantable medical devices, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

A potential shortcoming of the foregoing method of medicating stents is that the polymers can contain impurities that trigger adverse biological responses to the stent when implanted into a biological lumen. The polymers can contain impurities such as catalysts, initiators, processing aids, suspension aids, unreacted monomers and oligomers or other low molecular weight species, even though the polymer is sold as a "medical grade" polymer by the manufacturer. Thus, there is a need for a stent coating with purified polymers. The present invention provides a coating to meet this need.

SUMMARY

In accordance with one aspect of the invention, a stent is disclosed that is used for implantation in a vessel of a patient. The stent includes a coating which has a polymeric material which has been purified to be completely or partially free from an impurity or impurities which cause the material to have a greater adverse biological response than the response caused by the material when the impurity or impurities have been removed or reduced from the material. In one embodiment of the invention, the polymeric material is a polyacrylate material. In another embodiment, the polymeric material is a blend of at least two polymers. In a further embodiment, the coating additionally has an active agent.

In accordance with a further aspect of the invention, a method of coating a stent is disclosed, including forming a coating having a polymeric material on the stent, wherein the polymeric material has been purified to remove, or reduce the amount of, an impurity or impurities which cause the material to have a greater adverse biological response than the response caused by the material when the impurity or impurities have been removed or reduced from the material. In one embodiment, the polymeric material is purified by a process including solvent washing, centrifugal cleaning, soxhlet extraction, filtration, step precipitation, centrifugal filtration or a combination thereof.

In a further aspect, a method of coating a stent is disclosed including purifying a polymeric material to partially or completely remove an impurity or impurities which can cause an adverse biological response, adding the purified polymeric material to a solvent to form a composition, applying the composition to the stent, and removing the solvent to form a coating including the purified polymeric material.

In yet another aspect of the present invention, a stent is disclosed with a coating, the coating including a purified polymeric material that has generally the same degree of biological inertness as stainless steel when implanted in a blood vessel of a mammal.

DETAILED DESCRIPTION

Figure 1:
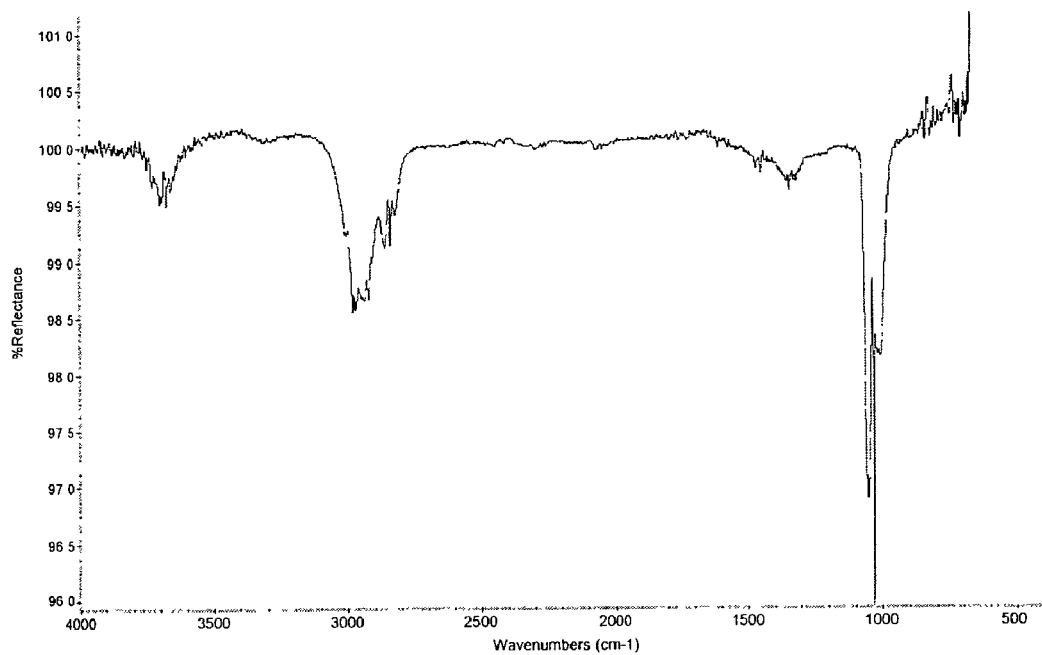
FIGS. 1-4 are comparative spectrographs from a Fourier Transform Infrared Spectrophotometer as referred to in Example 2.

For ease of discussion, the coatings and methods detailed herein will be described with reference to a coating for a stent. However, the implantable device coated in accordance with embodiments of the present invention may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), stainless steel (316L), "MP35N," "MP20N," elastinite (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Coating

In an embodiment of the present invention, a stent has a coating that includes a purified polymer. The polymer can be purified by methods detailed herein. The stent can be used for implantation at a selected region of a vessel of a patient for inhibiting restenosis, and can include an active agent. After the polymer has been purified, the polymer is substantially biologically inert. "Purified" refers to a polymer that has had impurities removed or significantly reduced. "Impurities" refer to traces of catalysts, initiators, processing aids, suspension aids, unreacted monomers and oligomers or other low molecular weight species, or any other chemical remaining in the polymer, that can cause or effectuate an adverse biological response greater than which would occur if the impurity is removed or significantly reduced. For example, "medical grade" poly(n-butyl methacrylate) (PBMA) can contain impurities such as suspension aids (e.g., starch) and unreacted monomers. "Biologically inert" refers to a material that does not elicit a significantly greater adverse biological response than a biocompatible material, such as stainless steel, when implanted into a body vessel. Examples of biocompatible materials include metals such as stainless steel, titanium, and Nitinol, and organic materials such as collagen, fibronectin, polyethylene glycol, polysaccharides, TEFLON, silicone and polyurethane. As shown below in Example 5, it has been found that the polymeric coating of the present invention is essentially biologically inert.

The coating for a stent including the purified polymer can have a drug-polymer layer, an optional topcoat layer, and an optional primer layer. The drug-polymer layer can be applied directly onto the stent surface to serve as a reservoir for a therapeutically active agent or drug which is incorporated into the drug-polymer layer. The topcoat layer, which can be essentially free from any therapeutic substances or drugs, serves as a rate limiting-membrane for controlling the rate of release of the drug. The optional primer layer can be applied between the stent and the drug-polymer layer to improve the adhesion of the drug-polymer layer to the stent.

According to one embodiment of the present invention, polymers of esters having the general formula (I):

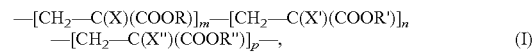

$$-[CH_2-C(X)(COOR)]_m-[CH_2-C(X')(COOR')]_n-[CH_2-C(X'')(COOR'')]_p-, \quad (I)$$

or blends thereof, can be purified and then used for making the stent coatings.

In formula (I), X, X', and X'' are each, independently, a hydrogen atom (acrylates) or an alkyl group, such as a methyl group $CH_3$ (methacrylates); R, R' and R'' are each, independently, a $C_1$ to $C_{12}$ straight chained or branched aliphatic group, or a hydroxylated aliphatic group; "m" is an integer larger than 1, and "n" and "p" are each 0 or an integer. If both n=0 and p=0, the polymer of formula (I) is a homopolymer (i.e., PBMA). If n≠0 and p=0, or n=0 and p≠0, the polymer of formula (I) is a copolymer, and if n≠0 and p≠0, the polymer of formula (I) is a terpolymer.

After purification, polymers of formula (I) can be used for making either the drug-polymer layer, the topcoat membrane, the optional primer layer, or any combination thereof. For the purposes of the present invention, such polymers, or blends thereof, are defined as "polyacrylates" or as "polyacrylate materials."

One example of a polyacrylate suitable for fabricating either the drug-polymer layer or the topcoat membrane is PBMA, described by formula (I) where $X=CH_3$, n=0, p=0, and "R" is a n-butyl radical $C_4H_9$ ($-CH_2-CH_2-CH_2-CH_3$). PBMA has good biocompatibility, is soluble in many common solvents, has good mechanical and physical properties, and adheres well to the underlying stent surface or the primer layer. PBMA is available commercially from Aldrich Chemical Co. of Milwaukee, Wis., and from Esschcm, Inc. of Lynwood, Pa.

Some examples of polyacrylates that are suitable for purification and fabrication of the coating, e.g., the drug-polymer layer and/or the topcoat membrane, are summarized in Table 1.

TABLE 1

| No. | Polyacrylate | Abbreviation | R | X | m | R' | X' | n/m | $T_g$, °C. |
|---|---|---|---|---|---|---|---|---|---|
| 1 | Poly(n-butyl methacrylate) | PBMA | n-$C_4H_9$ | $CH_3$ | >1 | N/A | N/A | 0 | 20 |
| 2 | Poly(iso-butyl methacrylate) | Pi-BMA | i-$C_4H_9$ | $CH_3$ | >1 | N/A | N/A | 0 | 66 |
| 3 | Poly(tert-butyl methacrylate) | Ptert-BMA | tert-$C_4H_9$ | $CH_3$ | >1 | N/A | N/A | 0 | 107 |
| 4 | Poly(methyl methacrylate) | PMMA | $CH_3$ | $CH_3$ | >1 | N/A | N/A | 0 | 105 |
| 5 | Poly(ethyl methacrylate) | PEMA | $C_2H_5$ | $CH_3$ | >1 | N/A | N/A | 0 | 63 |
| 6 | Poly(n-propyl methacrylate) | PPMA | n-$C_3H_7$ | $CH_3$ | >1 | N/A | N/A | 0 | 35 |
| 7 | Poly(methyl acrylate) | PMA | $CH_3$ | H | >1 | N/A | N/A | 0 | 9 |
| 8 | Poly(n-hexyl methacrylate) | PHMA | n-$C_6H_{13}$ | $CH_3$ | >1 | N/A | N/A | 0 | −5 |
| 9 | Poly(methyl methacrylate-co-n-butyl methacrylate) | P(MMA-BMA) | $CH_3$ | $CH_3$ | >1 | n-$C_4H_9$ | $CH_3$ | 7/3 | 46 |
| 10 | Poly(n-butyl methacrylate-co-iso-butyl methacrylate) | P(BMA-i-BMA) | n-$C_4H_9$ | $CH_3$ | >1 | i-$C_4H_9$ | $CH_3$ | 1/1 | 35 |
| 11 | Poly(n-butyl methacrylate-co-2-hydroxyethyl methacrylate) | P(BMA-HEMA) | n-$C_4H_9$ | $CH_3$ | >1 | $CH_2CH_2OH$ | $CH_3$ | 7/3 | ≧25 |
| 12 | Poly(methyl methacryate-co-2-hydroxyethyl methacrylate) | P(MMA-HEMA) | $CH_3$ | $CH_3$ | >1 | $CH_2CH_2OH$ | $CH_3$ | 7/3 | ≧65 |
| 13 | Poly(ethyl methacrylate-co-2-hydroxyethyl methacylate) | P(EMA-HEMA) | $C_2H_5$ | $CH_3$ | >1 | $CH_2CH_2OH$ | $CH_3$ | 7/3 | >50 |

Only homo- and copolymers are listed in Table 1 (that is, the polymers of formula (I) where p=0), but it should be understood that terpolymers corresponding to formula (I) (when n≠0 and p≠0) can be used as well. Also, it should be understood that the n/m ratios (from formula (I)) listed in Table 1 are provided by way of example, and other n/m ratios are contemplated to fall within the scope of this invention. For instance, the n/m ratio for P(BMA-HEMA) can also be 95/5.

Methods of Purification

Before the polymer is applied to the stent to form a coating, the polymer should be purified to remove impurities. By using the methods of the present invention, the polymer can be purified to remove a significant amount of residual catalysts, initiators, processing aids, suspension aids, unreacted monomers and oligomers or other low molecular weight species. For example, a polymer mass can be purified by washing the polymer mass with a solvent that dissolves the impurity, but not the polymer. Additionally, the polymer mass can be purified by dissolving the polymer mass in a solvent and subjecting the polymer mass to a centrifuge. According to other embodiments, the polymers can be purified by soxhlet extraction, filtration, step precipitation, and centrifugal filtration.

Solvent Washing

A solvent can be used to wash the impurities from the polymer. The impurities, such as low molecular species including unreacted monomers and oligomers, should be miscible in the solvent, while the polymer should be immiscible in the solvent. Representative examples of polymer-solvent pairs include using methanol for PBMA, ethanol for PMMA, acetonitrile or hexane for PEMA and methanol for P(BMA-HEMA).

The polymer should be mixed with the solvent and stirred. Sonication can also be used to mix the components. The polymer and solvent can be mixed for a few minutes to several hours, for example, from 1 to 16 hours. Usefully, the mixture is agitated for a relatively longer period to remove certain impurities. The mixed solvent can be replaced by fresh solvent so that the polymer can be washed multiple times. After the washing process is complete, the polymer is then dried (e.g., by vacuum drying) to remove the solvent from the polymer.

Centrifugal Cleaning

The polymer can also be purified by using a centrifuge if the impurity has a higher density than the polymer solution. The polymer is first substantially dissolved in a solvent. By way of example, PBMA can be dissolved in acetone. Usefully, for many polymers, the solvent is a low density solvent (e.g., tetrahydrofuran (THF) or ethyl acetate). Many high density solvents such as chloroform, may not be useful for this particular process. Representative examples of polymer-solvent pairs include using ethyl acetate for PEMA, methyl ethyl ketone for PMMA and THF for P(BMA-HEMA).

After the polymer is dissolved in the solvent, the solution is centrifuged for about 10 minutes to 1 hour. The supernatant is carefully collected and the precipitate at the bottom of the centrifuge tubing, which contains impurities, is then removed from the solution. It is preferred that the solvent used for this process is the same solvent used for the stent coating process described in detail below. Also, it is preferred to use this centrifugal cleaning process subsequent to the solvent washing process.

Filtration

Instead of using a centrifuge, impurities can be removed from the polymer by using filtration. The polymer should first be substantially dissolved in a solvent. The solvents useful for the centrifugal cleaning process are also useful for this process. The solution is then run through a filter connected to a vacuum pump to remove the impurities that do not dissolve with the polymer. The filter used should have a pore size large enough to allow the passage of the polymer, but small enough to remove the impurities from the solution. Representative examples of pore sizes for filters include 1-10 μm.

Soxhlet Extraction

A soxhlet extraction can also be used to remove impurities from the polymer, especially if the $T_g$ of the polymer is relatively high (e.g., Pi-BMA, PMMA and PEMA). First, a polymer is placed into a glass extraction tube and the tube is placed inside an extraction apparatus. A solvent is mixed with the polymer. The solvent should be incompatible with the polymer (i.e., does not dissolve the polymer), but should be compatible with one or more impurities. The solvent may cause the polymer to partially swell. Also, typically, the solvent will have a boiling temperature that is below or equal to the $T_g$ of the polymer. In this process, the solvent serves as the extraction medium. Representative examples of polymer-solvent pairs include using methanol for Pi-BMA, ethanol or acetonitrile:methanol (50:50 wt/wt) for PMMA, hexane for PEMA and FLUX REMOVER AMS for P(BMA-HEMA). After the polymer has been put into solution, a heating source is used to warm the solvent to generate vapor. The solvent vapor removes low molecular weight species from the polymer.

It has been found that if the temperature exposed to the extraction apparatus is too close to the $T_g$ of the polymer, the polymer can swell and block the filters used in the extraction apparatus. As a result, it may be useful to cool portions of the extraction apparatus (e.g., extraction tube) during the process to prevent polymer swelling.

Step Precipitation

The polymer can also be purified by using a step precipitation process. A polymer mass should first be substantially dissolved in a compatible solvent. While the solution is stirred, an incompatible solvent is gradually added to the solution so that polymer precipitates. The polymer is then recovered and dried. The impurities that were in the polymer before the process remain in the solution. In an embodiment, step precipitation is used after centrifugal cleaning wherein the polymer remains dissolved in the solvent used for the centrifugal cleaning process before addition of the incompatible solvents. The following are representative examples of polymer-solvent pairings:

TABLE 2

| Polymer | Compatible Solvent(s) | Incompatible Solvent(s) |
| --- | --- | --- |
| PBMA | Acetone | Water or Heptane |
| PEMA | THF | Methanol |
| P(BMA-HEMA) | THF | Water |

Centrifugal Filtration

Impurities can also be removed by centrifugal filtration. This method was originally developed for the removal of cells and particulates from nucleic acids, proteins, and enzymes, and has been adapted for the present invention to remove lower molecular weight fractions from a polymer. First, the polymer is dissolved in a solvent. Then the solution is placed in a centrifugal filtration unit (such as Centriplus-100, available from Millipore, Medford, Mass.) which is run in a centrifuge (e.g., available from Sorvall, Newtown, Conn.). The filtration unit should be compatible with the solvent used to dissolve the polymer. In one embodiment, the polymer is first subjected to the centrifugal cleaning process, and then further purified by being placed in the centrifugal filtration apparatus.

Method of Forming the Coating

To fabricate the coating, the purified polymer, or a blend of purified polymers, can be applied on the stent using commonly used techniques known to those having ordinary skill in the art. For example, the polymer can be applied to the stent by dissolving the polymer in a coating solvent, or a mixture of solvents, and applying the resulting solution on the stent by spraying or immersing the stent in the solution.

Representative examples of some suitable coating solvents include N,N-dimethylacetamide (DMAC), N,N-dimethylformamide (DMF), tethrahydrofurane (THF), cyclohexanone, xylene, toluene, acetone, methyl ethyl ketone, propylene glycol monomethyl ether, methyl butyl ketone, ethyl acetate, n-butylacetate, and dioxane. Examples of suitable mixtures of solvents include mixtures of DMAC and methanol (e.g., a 50:50 by mass mixture), cyclohexanone and acetone (e.g., 80:20, 50:50, or 20:80 by mass mixtures), acetone and xylene (e.g., 50:50 by mass mixture), and acetone, FLUX REMOVER AMS, and xylene (e.g., 10:50:40 by mass mixture). FLUX REMOVER AMS is a trade name of a solvent manufactured by Tech Spray, Inc. of Amarillo, Tex. comprising about 93.7% of a mixture of 3,3-dichloro-1,1,1,2,2-pentafluoropropane, 1,3-dichloro-1,1,2,2,3-pentafluoropropane, and the balance methanol, with trace amounts of nitromethane.

In addition, blends of polymers can be used to fabricate the coating. In one embodiment, blends of polyacrylates, such as those listed in Table 1, can be used to fabricate the coating. In another embodiment, a blend of polyacrylates with non-acrylate materials is used. Poly(ethylene-co-vinyl alcohol) (EVAL) is one example of a suitable non-acrylate polymer. EVAL has the general formula $—[CH_2—CH_2]_q—[CH_2—CH(OH)]_r—$, where "q" and "r" are each an integer. EVAL may also include up to 5 molar % of units derived from styrene, propylene and other suitable unsaturated monomers. A brand of copolymer of ethylene and vinyl alcohol distributed commercially under the trade name EVAL by Aldrich Chemical Co., or manufactured by EVAL Company of America of Lisle, Ill., can be used.

Examples of other polymers with which polyacrylates can be blended include fluorinated polymers, such as poly(vinylidene fluoride) (PVDF) and poly(vinylidene fluoride-co-hexafluoro propene) (PVDF-HFP). The blend of a polyacrylate and a fluorinated polymer can contain between about 10 and about 95% (mass) of the fluorinated polymer.

Additionally, polymers other than polyacrylates can be used for the coating. Representative examples of suitable alternative polymers include EVAL, poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane; poly(amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

The active agent or drug can include any substance capable of exerting a therapeutic or prophylactic effect for a patient. The drug may include small molecule drugs, peptides, proteins, oligonucleotides, and the like. The active agent could be selected, for example, to inhibit the activity of vascular smooth muscle cells. It can be directed at inhibiting abnormal or inappropriate migration and/or proliferation of smooth muscle cells to inhibit restenosis. Examples of drugs include immunosuppressive substances such as rapamycin and structural derivatives or functional analogs thereof, such as 40-O-(2-hydroxy)ethyl-rapamycin (known by the trade name of everolimus available from Novartis), 40-O-tetrazole-rapamycin, 40-O-(3-hydroxy)propyl-rapamycin and 40-O-[2-(2-hydroxy)ethoxy]ethyl-rapamycin; and antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin, hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon; genetically engineered epithelial cells; tacrolimus; and dexamethasone.

EXAMPLES

Some embodiments of the present invention are illustrated by the following Examples.

Example 1

About 15 grams of PBMA (medical grade, Lot PB 2375 from Esstech, Inc.) was combined with about 185 grams of HPLC grade methanol (available from Aldrich Chemical Co.). The mixture was stirred rigorously for 3 hours, and then the methanol was removed. This procedure was repeated for 5 cycles. After the last cycle, the polymer was vacuum dried at room temperature for about 24 hours to remove residual methanol.

Example 2

Figure 2:
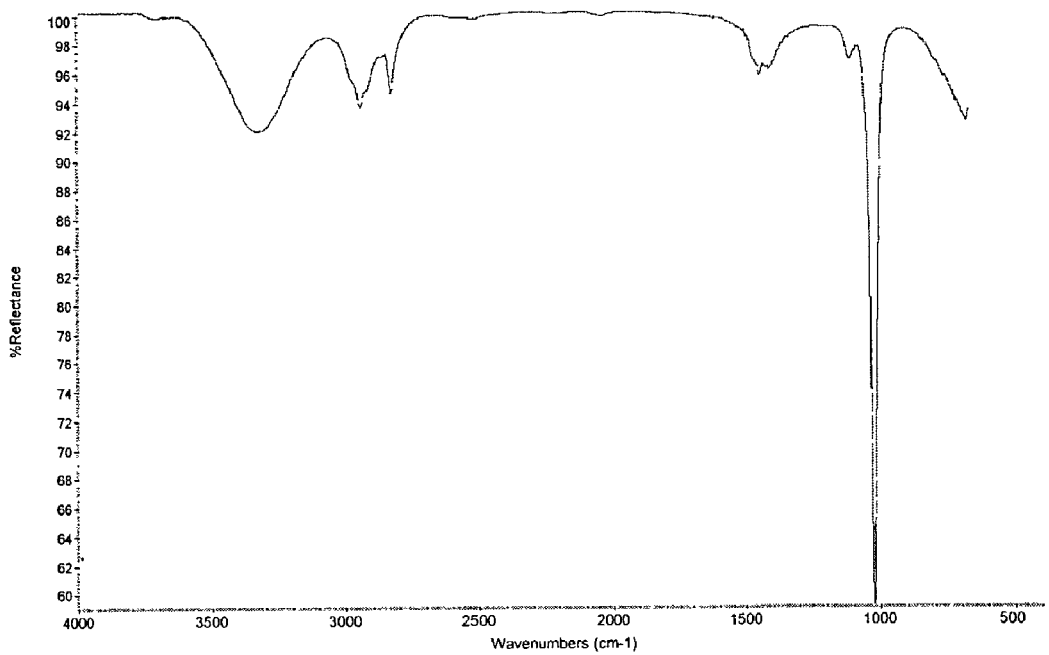
Figure 3:
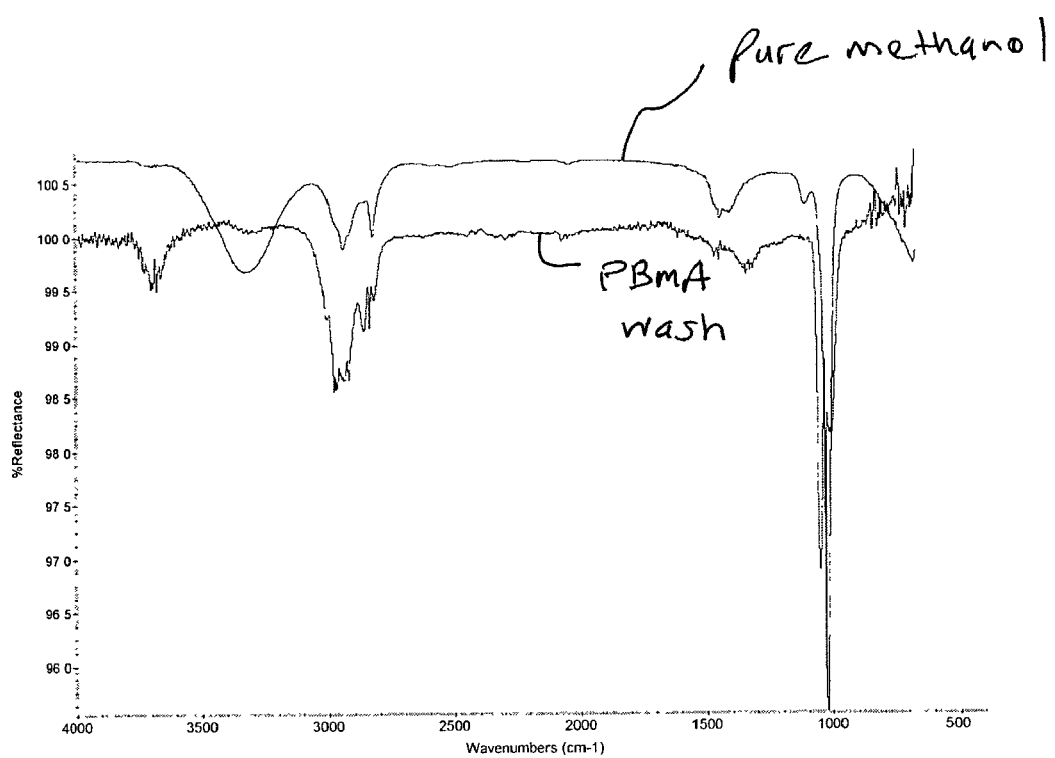
Figure 4:
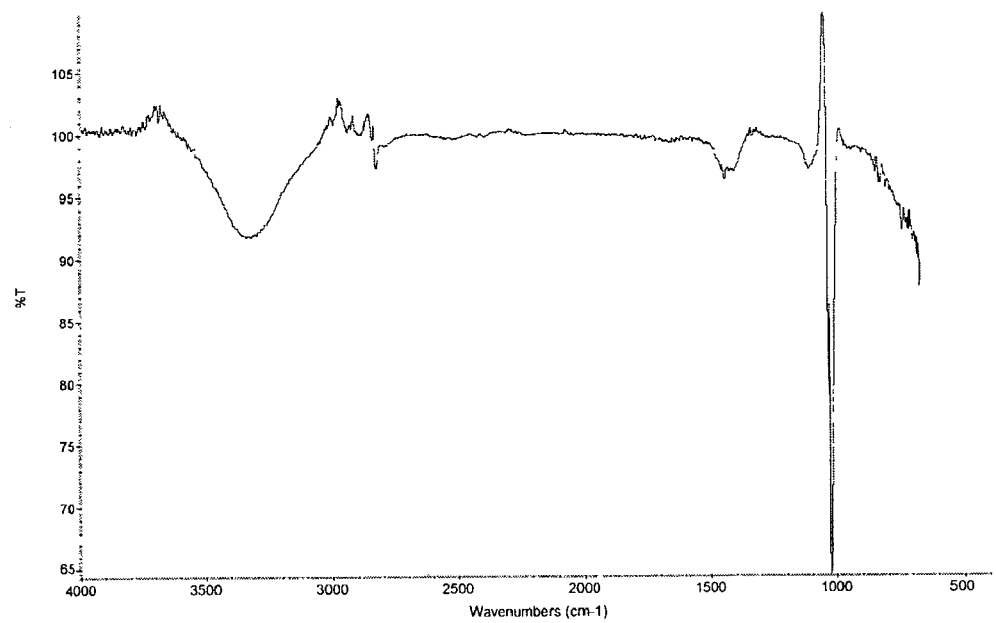

A sample of methanol from Example 1 that was removed after washing the polymer was studied to determine if impurities had been removed from the polymer. In particular, a Fourier Transform Infrared Spectrophotometer (available from Perkin-Elmer, Wellesley, Mass.) was used to compare the spectra from the removed methanol to the spectra of HPLC grade methanol (available from Aldrich Chemical Co.). Referring to FIG. 1, the spectra for the PBMA wash had peaks at 1033 and 1053 cm−1. As shown in FIG. 2, however, the spectra for the pure methanol had a peak at 1029 cm−1. FIG. 3 is an overlay of the two spectra, while FIG. 4 is a subtraction of the two spectra showing that there is a significant peak difference at 1029 cm−1. In short, FIG. 4 indicates that an impurity was washed from the polymer in Example 1.

Example 3

The purified polymer from Example 1 was dissolved in acetone (>99.5% purity, Class 10, Lot C01101, available from General Chemical Corporation, Detroit, Mich.) at 15% wt/wt. The solution was placed into a 50 ml centrifuge tube and run in a Model 225 Fisher Scientific Centrifuge (available from Fisher Scientific, Houston, Tex.). The centrifuge was set at a RPM setting of 6 and was run for about 30 minutes. The precipitate containing the impurities was collected and the solution was visually clean. The supernatant was then collected.

Example 4

The purified polymer (i.e., supernatant) from Example 3 was diluted to 2% PBMA in 80:20 acetone/cyclohexanone wt/wt to produce a coating composition. 3×13 mm TETRA stents (available from Guidant Corporation) were provided which are made of stainless steel. The stents were cleaned by sonicating for several minutes in de-ionized-water, methanol, then IPA. The stents underwent argon plasma treatment just before being coated.

Thirty-five 3×13 mm TETRA stents were coated with the purified polymer composition under the following conditions using a spray coater with an EFD 780S series nozzle: atomization pressure=about 8 psi; feeding pressure=about 3.95 psi; rotation speed=about 60 rpm; no translation motion; nozzle-to-stent distance=about 4.5 cm; spray time=about 2 sec; and waiting until next spray cycle=about 8 sec. After a number of spray cycles, the stents were dried at 70° C. for one hour to essentially remove the solvent and form a coating.

12 of the coated stents and 8 bare metal TETRA stents were then crimped onto a balloon catheter apparatus. The stents along with the balloon catheters were then sterilized by ETO for about 12 hours and then aerated for about 48 hours.

Example 5

9 of the coated stents and 5 of the bare metal stents from Example 4 were used to conduct an animal study. In particular, a 28 day porcine coronary artery model was used to determine if there was a significant biological response from the implantation of PBMA purified according to the methods of the present invention as compared to bare metal (i.e., stainless steel) stents. A standard implantation procedure was used to develop the histology data.

After the stented arteries were removed, they were processed using standard techniques to produce histology slides. Three sections of the stented vessels (i.e., proximal, media and distal) were used in the histology analysis. The percent stenosis was measured. The following Table 3 summarizes the histology data. The data is shown graphically in FIG. 5, and FIG. 6 (bare metal stents) and 7 (PBMA coated stents) are sample histology photographs produced by the study.

TABLE 3

| Bare Metal Stents | % Stenosis | Purified PBMA Coated Stents | % Stenosis |
|---|---|---|---|
| 1 | 46.20 | 1 | 32.18 |
| 2 | 28.16 | 2 | 23.36 |
| 3 | 22.52 | 3 | 32.07 |
| 4 | 16.91 | 4 | 17.95 |
| 5 | 23.05 | 5 | 18.09 |
|   |   | 6 | 26.61 |
|   |   | 7 | 42.75 |
|   |   | 8 | 24.64 |
|   |   | 9 | 26.05 |
| Average % Stenosis | 27.37 |   | 27.08 |
| Standard Deviation | 11.26 |   | 7.76 |

Figure 5:
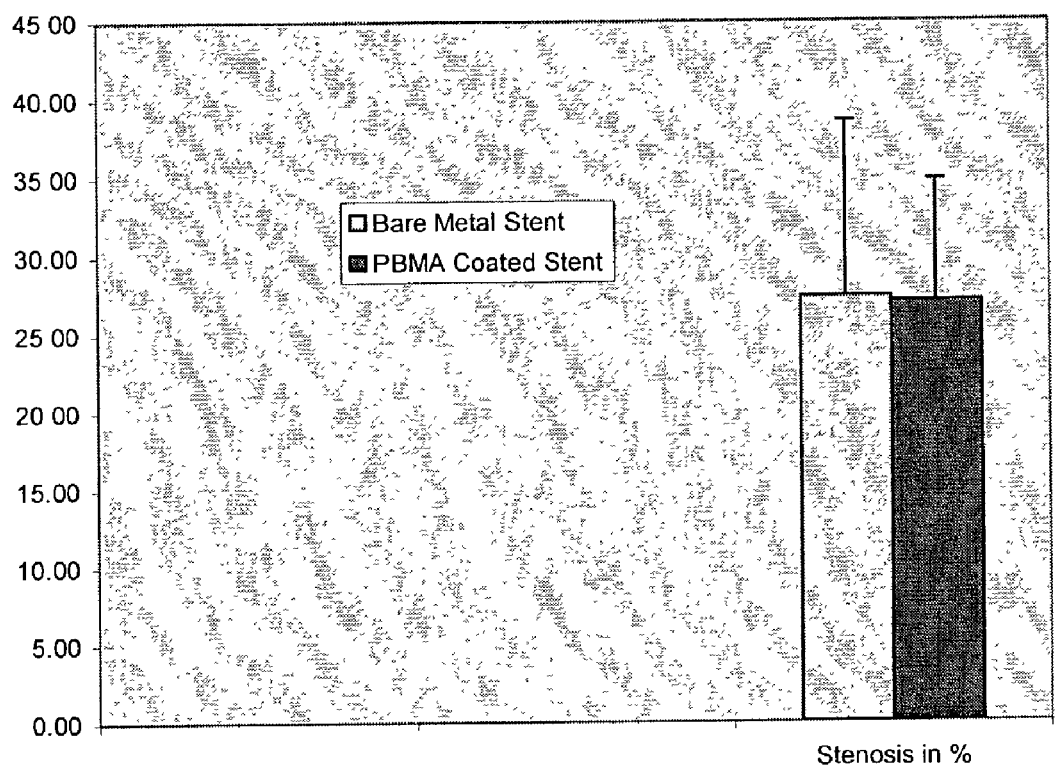
FIG. 5 is a graph of percent stenosis from a 28 day animal study as referred to in Example 5.
Figure 6:
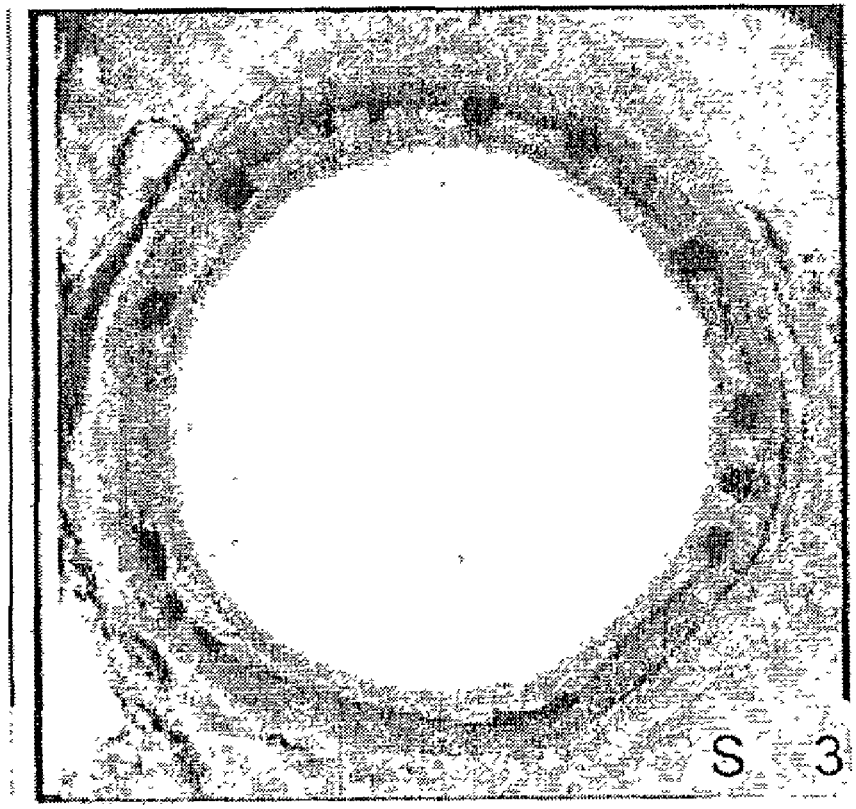
FIGS. 6 and 7 are histograms as referred to in Example 5.
Figure 7:
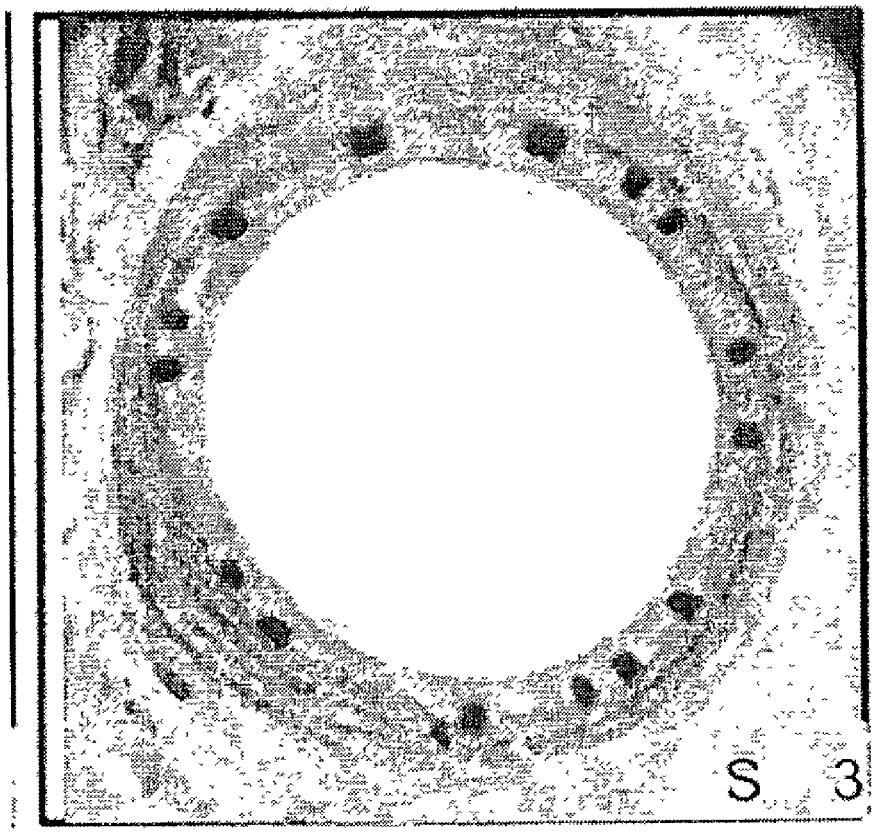

As shown in the data of Table 3, and FIG. 5, the area stenosis after 28 days as a result of an implantation of a stent with a purified polymer is substantially equivalent to the area stenosis after 28 days for a stent made of a biocompatible metal. Therefore, the purified polymer was shown to be biologically inert.

Example 6

PBMA ($M_w$=370K) is dissolved in acetone at 1 gram of PBMA per 5 grams of acetone (wt/wt). The polymer can be agitated or left at room temperature for a number of hours until the polymer become essentially dissolved in the solvent. Some of the low-density particles/aggregates (e.g., suspension agents) may become visible in the solution. The solution can then be exposed to vacuum filtration. The pore size of the filters can be from about 3 μm to about 10 μm.

Example 7

PBMA ($M_w$=370K) is dissolved in acetone at 1:7 (wt/wt). Drops of water/methanol (1:1 wt/wt) are slowly added into the solution while stirring until the rate of polymer precipitation decreases. The precipitated polymer is then recovered and vacuum-dried at 65° C. for 36 hours. The recovered polymer is then re-dissolved in xylene at 20% (wt/wt) for spray application.

Example 8

PBMA ($M_w$=370K) is dissolved in ethyl acetate at 15% wt/wt. The solution is placed in a Fisher Scientific Centrifuge, and the centrifuge is run for 30 minutes at a RPM setting of 6. The supernatant is collected. A portion of the supernatant is further diluted to 3% wt/wt and is transferred to a centrifugal filtration unit (available from Millipore). The centrifuge spin speed is set at 9.5 and the solution is centrifuged for about 4 hours. The process can be repeated. After about 24 hours of centrifugal filtration, a significant amount of the purified polymer can be collected.

Example 9

A polymer solution is prepared containing about 2.0 mass % of EVAL in DMAC. The solution is applied onto a stent to form a primer layer. To apply the primer layer, a spray apparatus such as the EFD 780S spray nozzle with a VALVEMATE 7040 control system, manufactured by EFD, Inc. of East Providence, Rhode Island is used. The EFD 780S spray nozzle is an air-assisted external mixing atomizer. The composition is atomized by air and applied to the stent surfaces. During the process of applying the composition, the stent is rotated about its longitudinal axis at a speed of about 100 rpm. The stent is also linearly moved along the same axis during the application.

The EVAL solution is applied to a 13-mm TETRA stent (available from Guidant Corporation) in a series of 10-second passes to deposit about 10 μg of coating per spray pass. Between the spray passes, the stent is dried for about 10 seconds using flowing air with a temperature of about 60° C. Five spray passes are applied, followed by baking the primer layer at about 140° C. for one hour. As a result, a primer layer is formed having a solid content of about 50 μg. "Solid" means the amount of the dry residue deposited on the stent after essentially all volatile organic compounds (e.g., the solvent) have been removed.

A drug-containing formulation is prepared comprising:
(a) about 2.0 mass % of EVAL;
(b) about 1.0 mass % of everolimus; and
(c) the balance, a solvent mixture of DMAC and pentane, the solvent mixture containing about 80 (mass) % of DMAC and about 20 (mass) % of pentane.

In a manner identical to the application of the primer layer, five spray passes are performed, followed by baking the drug-polymer layer at about 50° C. for about 2 hours to form the drug-polymer layer having a solid content of about 90 μg and a drug content of about 30 μg.

Finally, a topcoat composition to control the drug release rate is prepared having purified PBMA. The PBMA polymer used for this example is first purified by solvent washing using methanol, and then centrifugal cleaning using acetone. The purified PBMA is then added to a solvent system and diluted to provide a 2.0 mass % solution, where the solvent system includes a 10:50:40 (mass) blend of acetone, Techspray's FLUX REMOVER AMS, and xylene. In a manner similar to the application of the primer layer and the drug-polymer layer, a number of spray passes are performed followed by final baking at about 50° C. for about 2 hours. As a result, a purified topcoat membrane is formed, the membrane having a solid content of about 50 μg.

Example 10

A primer layer is applied onto an 18-mm TETRA stent using PBMA purified by solvent washing using methanol followed by centrifugal cleaning using acetone. A drug formulation is prepared comprising:
(a) about 2.0 mass % of PBMA also purified by solvent washing using methanol followed by centrifugal cleaning using acetone;
(b) about 1.6 mass % of everolimus; and
(c) the balance, a solvent system having a 60:40 (mass) blend of acetone and xylene.

The drug formulation is applied onto the stent and a drug-polymer layer is formed in a manner similar to that described in Example 9. The solid content of the drug-polymer layer is about 1,000 μg. In this Example, the stent coating does not have a separate topcoat membrane.

Example 11

A primer layer is applied onto an 18-mm TETRA stent as described in Example 10. A drug formulation is then prepared including:
(a) about 2.0 mass % of P(MMA-BMA) having a weight-average molecular weight ($M_w$) of about 150,000 available from Aldrich Chemical Company. Before the P(MMA-BMA) polymer is added to the formulation, the polymer is purified by first washing with methanol and then extracting with soxhlet extraction using Techspray's FLUX REMOVER AMS for about 12 hours;
(b) about 1.0 mass % of everolimus; and
(c) the balance, a solvent system including a 10:50:40 (mass) blend of acetone, FLUX REMOVER AMS and xylene.

The P(MMA-BMA) contains about 79.2 mass % of units derived from BMA. The drug formulation is applied onto the dried primer layer in a manner similar to that described in Example 9, to form a drug polymer layer. The drug-polymer layer has the total amount of solid of about 520 μg. In this Example, the stent coating does not have a separate topcoat membrane.

Example 12

A primer layer and a drug-polymer layer are applied onto an 18-mm TETRA stent as described in Example 9. A blend of P(MMA-BMA) and PBMA is then purified by washing in methanol and then centrifugal cleaning with acetone as the solvent. A topcoat composition to control the drug release rate is prepared having about 2.0 mass % of a 1:1 (by mass) blend of purified P(MMA-BMA) and PBMA, and the balance solvent system. The solvent system includes a 10:50:40 (mass) blend of acetone, FLUX REMOVER AMS and xylene. The P(MMA-BMA)/PBMA blend can have about 83.3 mass % of units derived from BMA. The topcoat membrane is formed having a total amount of solid of about 30 μg.

Example 13

A primer layer is applied onto an 18-mm TETRA stent as described in Example 10. A drug formulation is then prepared including:
(a) about 2.0 mass % of PBMA-HEMA (n/m=7/3). Before the PBMA-HEMA polymer is added to the formulation, the polymer is purified by first washing with methanol and then centrifugal cleaning using acetone;
(b) about 1.6 mass % of everolimus; and
(c) the balance, a solvent system including a 70:30 (mass) blend of acetone and xylene.

The drug formulation is applied onto the dried primer layer to form the drug-polymer layer. The drug-polymer layer has a total amount of solid of about 600 μg. In this Example, the stent coating does not have a separate topcoat membrane.

Example 14

A primer layer and a drug-polymer layer are applied onto an 18-mm TETRA stent as described in Example 9. A select amount of PEMA is then purified by first washing with methanol and then extracting with soxhlet extraction using FLUX REMOVER AMS for about 12 hours. A topcoat composition is prepared to control the drug release rate having about 2.0 mass % of purified PEMA, and the balance, a solvent system including a 80:20 (mass) blend of acetone and cyclohexanone. PEMA having a weight-average molecular weight $M_w$ of about 101,400 available from Aldrich Chemical Company is one example of a brand of PEMA that can be used.

The topcoat composition is applied onto the dried drug-polymer layer. A number of spray passes are performed followed by final baking, at about 80° C. for about 1 hour. The topcoat membrane is formed having a solid content of about 40 µg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent for implantation in a vessel of a patient, comprising a coating, the coating including a purified polymeric material which is completely or partially free from an impurity or impurities which cause the material to have a greater adverse biological response than the response caused by the material when the impurity or impurities have been removed or reduced from the material wherein the coating includes at least two layers, wherein at least one of the layers includes an active agent for the treatment of restenosis, wherein at least one of the layers includes the purified polymeric material, and wherein the purified polymeric material includes a polyacrylate material.

2. The stent of claim 1, wherein the active agent is rapamycin, everolimus or derivatives or analogs of rapamycin or everolimus.

3. The stent of claim 1, wherein the polymeric material prior to purification is a medical grade polymer as sold by the manufacturer.

4. The stent of claim 1, wherein the polymeric material is purified by a process selected from the group consisting of solvent washing, centrifugal cleaning, soxhlet extraction, filtration, step precipitation, centrifugal filtration or a combination thereof.

5. The stent of claim 1, wherein the purified polymeric material has generally the same degree of biological inertness as stainless steel.

6. A stent for implantation in a vessel of a patient, comprising a coating, the coating including a purified polymeric material which is completely or partially free from an impurity or impurities which cause the material to have a greater adverse biological response than the response caused by the material when the impurity or impurities have been removed or reduced from the material, wherein the polymeric material includes poly(butyl methacrylate) and the coating additionally comprises rapamycin or functional analog or structural derivative thereof.

7. The stent of claim 6, wherein the coating includes at least two layers, wherein the outer most layer of the coating is made from the purified polymeric material.

8. The stent of claim 6, wherein the polymeric material is a blend of at least two polymers.

9. The stent of claim 6, wherein the polymeric material prior to purification is a medical grade polymer as sold by the manufacturer.

10. The stent of claim 6, wherein the polymeric material is purified by a process selected from the group consisting of solvent washing, centrifugal cleaning, soxhlet extraction, filtration, step precipitation, centrifugal filtration or a combination thereof.

11. The stent of claim 6, wherein the purified polymeric material has generally the same degree of biological inertness as stainless steel.

12. A stent used for implantation in a vessel of a patient, comprising a coating, the coating including a purified medical grade polymeric material which is completely or partially free from an impurity or impurities which cause the material to have a greater adverse biological response than the response caused by the material when the impurity or impurities have been removed or reduced from the material.

13. The stent of claim 12, wherein the polymeric material is selected from a group consisting of poly(n-butyl methacrylate), poly(iso-butyl methacrylate), poly(tert-butyl methacrylate), poly(methyl methacrylate), poly(ethyl methacrylate), poly(n-propyl methacrylate), poly(methyl acrylate), poly(n-hexyl methacrylate), poly(methyl methacrylate-co-n-butyl methacrylate), poly(n-butyl methacrylate-co-iso-butyl methacrylate), poly(n-butyl methacrylate-co-2-hydroxyethyl methacrylate), poly(methyl methacrylate-co-2-hydroxyethyl methacrylate) and poly(ethyl methacrylate-co-2-hydroxyethyl methacylate).

14. The stent of claim 12, wherein the polymeric material is a polyacrylate material.

15. The stent of claim 12, wherein the coating includes at least two layers, wherein the outer most layer of the coating is made from the purified polymeric material.

16. The stent of claim 12, wherein the coating includes at least two layers, wherein at least one of the layers includes an active agent for the treatment of restenosis, wherein at least one of the layers is made from the purified polymeric material, and wherein the purified polymeric material includes a polyacrylate material.

17. The stent of claim 12, wherein the polymeric material includes poly(butyl methacrylate) and the coating additionally comprises rapamycin.

18. The stent of claim 12, wherein the coating additionally comprises an active agent.

19. The stent of claim 18, wherein the active agent is rapamycin, everolimus or derivatives or analogs of rapamycin or everolimus.

20. The stent of claim 12, wherein the polymeric material is a blend of at least two polymers.

21. The stent of claim 12, wherein the purified polymeric material has generally the same degree of biological inertness as stainless steel.

22. The stent of claim 12, wherein the polymeric material is a medical degrade polymer that is not purified as supplied by the manufacturer and prior to being coated on the stent.

23. A stent comprising a coating, the coating including a purified version of a medical grade polymeric material that has generally the same degree of biological inertness as stainless steel when implanted in a blood vessel of a mammal.

* * * * *